United States Patent
Abdulhalim

(10) Patent No.: US 9,518,926 B2
(45) Date of Patent: Dec. 13, 2016

(54) OPTICAL SENSOR WITH ENHANCED SENSITIVITY

(75) Inventor: Ibrahim Abdulhalim, Neve Shalom (IL)

(73) Assignee: Ben-Gurion University of the Negev Research & Development Authority, Beer Sheva (IL)

(*) Notice: Subject to any disclaimer, the term of this patent is extended or adjusted under 35 U.S.C. 154(b) by 744 days.

(21) Appl. No.: 13/985,509

(22) PCT Filed: Feb. 14, 2012

(86) PCT No.: PCT/IL2012/000075
§ 371 (c)(1),
(2), (4) Date: Aug. 14, 2013

(87) PCT Pub. No.: WO2012/111001
PCT Pub. Date: Aug. 23, 2012

(65) Prior Publication Data
US 2013/0323858 A1    Dec. 5, 2013

Related U.S. Application Data

(60) Provisional application No. 61/442,318, filed on Feb. 14, 2011.

(51) Int. Cl.
*G01N 33/553* (2006.01)
*G01N 21/65* (2006.01)
*G01N 21/552* (2014.01)
*G01N 33/543* (2006.01)

(52) U.S. Cl.
CPC .......... *G01N 21/658* (2013.01); *G01N 21/554* (2013.01); *G01N 33/54373* (2013.01)

(58) Field of Classification Search
None
See application file for complete search history.

(56) References Cited

U.S. PATENT DOCUMENTS

| | | | |
|---|---|---|---|
| 7,471,852 B2* | 12/2008 | Hamada | G02F 1/011 385/2 |
| 8,094,314 B2* | 1/2012 | Tetz | G01N 21/554 356/445 |
| 8,514,398 B2* | 8/2013 | Pang | G03H 1/02 250/286 |

(Continued)

OTHER PUBLICATIONS

Abdulhalim et al., "Surface Plasmon Resonance for Biosensing: A Mini-Review", Electromagnetics (2008), vol. 28, No. 3, pp. 214-242 (Abstract only).

(Continued)

*Primary Examiner* — Chris L Chin
(74) *Attorney, Agent, or Firm* — Hunton & Williams LLP

(57) ABSTRACT

The invention is a surface plasmon resonance (SPR) sensor to determine the presence and quantity of biological or chemical entities in an analyte. The sensor comprises a metal periodic structure deposited as a thin layer of a noble metal, comprising a one dimensional array of nanoslits or a two dimensional array of nanoholes on a transparent dielectric substrate, a nm-thick layer of transparent dielectric protection layer on top of the metal periodic structure and a functionalization layer, which acts as a binding layer to biological or biochemical entities in an analyte that is in contact with the functionaliztion layer.

16 Claims, 12 Drawing Sheets

(56) References Cited

U.S. PATENT DOCUMENTS

| | | | |
|---|---|---|---|
| 2005/0031278 A1* | 2/2005 | Shi | G02B 6/262 385/121 |
| 2008/0280374 A1 | 11/2008 | Potyrailo et al. | |
| 2009/0236614 A1 | 9/2009 | Puscasu et al. | |
| 2010/0256016 A1* | 10/2010 | Blair | B82Y 15/00 506/13 |
| 2011/0301066 A1 | 12/2011 | Blair | |

OTHER PUBLICATIONS

Abdulhalim, I., "Biosensing Configurations Using Guided Wave Resonant Structures" NATO Science for Peace and Security Series (2008), Chap. 9, pp. 211-228 (Abstract only).

Bethe, H.A., "Theory of Diffraction by Small Holes", Phys. Rev. (1944), vol. 66, No. 7-8, pp. 163-182 (Abstract only).

Brolo et al., "Surface plasmon sensor based on the enhanced light transmission through arrays of nanoholes in gold films." Langmuir (2004), vol. 20, No. 12, pp. 4813-4815 (Abstract only).

Cao et al., "Negative Role of Surface Plasmons in the Transmission of Metallic Gratings with Very Narrow Slits", Physical Review Letters (2002), vol. 88, No. 5 (4 pp).

Ding et al., "Improved SPR technique for determination of the thickness and optical constants of thin metal films", Optical and Quantum Electronics (2003), vol. 35, No. 12, pp. 1091-1097 (Abstract only).

Ebbesen et al., "Extraordinary optical transmission through sub-wavelength hole arrays", Nature (1998), vol. 391, pp. 667-669.

Fan et al., "Enhanced Infrared Transmission through Subwavelength Coaxial Metallic Arrays", Physical Review Letters (2005), vol. 94, No. 3, pp. 033902 (4 pp) (Abstract only).

Garcia-Vidal et al., "Multiple paths to enhance optical transmission through a single subwavelength slit.", Physical Review Letters (2003), vol. 90, No. 21, pp. 213901 (Abstract only).

Homola et al., "Surface plasmon resonance sensors: review", Sensors and Actuators B: Chemical (1999), vol. 54, Nos. 1-2, pp. 3-15 (Abstract only).

Hooper et al., "Differential ellipsometric surface plasmon resonance sensors with liquid crystal polarization modulators", Applied Physics Letters (2004), vol. 85, No. 15 (Abstract only).

Hsu et al., "Ellipsometric surface plasmon resonance", Journal of Biomedical Optics (2009), vol. 14, No. 2, pp. 024036 (Abstract only).

Karabchevsky et al., "Metal grating on a substrate nanostructure for sensor applications", Photonics and Nanostructures—Fundamentals and Applications (2009), vol. 7, pp. 170-175.

Karabchevsky et al., "Theoretical and Experimental Investigation of Enhanced Transmission Through Periodic Metal Nanoslits for Sensing in Water Environment", Plasmonics (2009), vol. 4, pp. 281-292.

Karabchevsky et al., "Dual-surface plasmon excitation with thin metallic nanoslits", Journal of Nanophotonics (2011), vol. 5, pp. 051821-1 through 051821-9.

Krasnykov et al., "Sensor with increased sensitivity based on enhanced optical transmission in the infrared", Optics Communications (2011), vol. 284, No. 5, pp. 1435-1438 (Abstract only).

Lee et al., "Sensitive biosensor array using surface plasmon resonance on metallic nanoslits", J. Biomed. Opt. (2007), vol. 12, No. 4, pp. 044023 (Abstract only).

Lee et al., "Comparisons of Surface Plasmon Sensitivities in Periodic Gold Nanostructures", Plasmonics (2008), vol. 3, No. 4, pp. 119-125 (Abstract only).

Liedberg et al., "Surface plasmon resonance for gas detection and biosensing", Sensors and Actuators (1983), vol. 4, pp. 299-304 (Abstract only).

Ma et al., "Guided-mode resonant grating filter with an antireflective surface for the multiple channels", Journal of Optics A: Pure and Applied Optics (2008), vol. 10, No. 2, pp. 025302 (Abstract only).

Rajan et al., "Fabrication and characterization of a surface plasmon resonance based fiber-optic sensor for bittering component—Naringin", Sensors and Actuators B: Chemical (2006), vol. 115, No. 1, pp. 344-348 (Abstract only).

Shalabney et al., "Electromagnetic fields distribution in multilayer thin film structures and the origin of sensitivity enhancement in surface plasmon resonance sensors", Sensors and Actuators A: Physical (2010), vol. 159, No. 1, pp. 24-32 (Abstract only).

Handbook of Biosensors and Biochips, (Marks et al., eds.) vol. 2, 2007, pp. 413-446, ISBN978-0-470-01905-4 (TOC only).

International Search Report issued in PCT/IL2012/000075, mailed on Aug. 16, 2012 (3 pp).

* cited by examiner

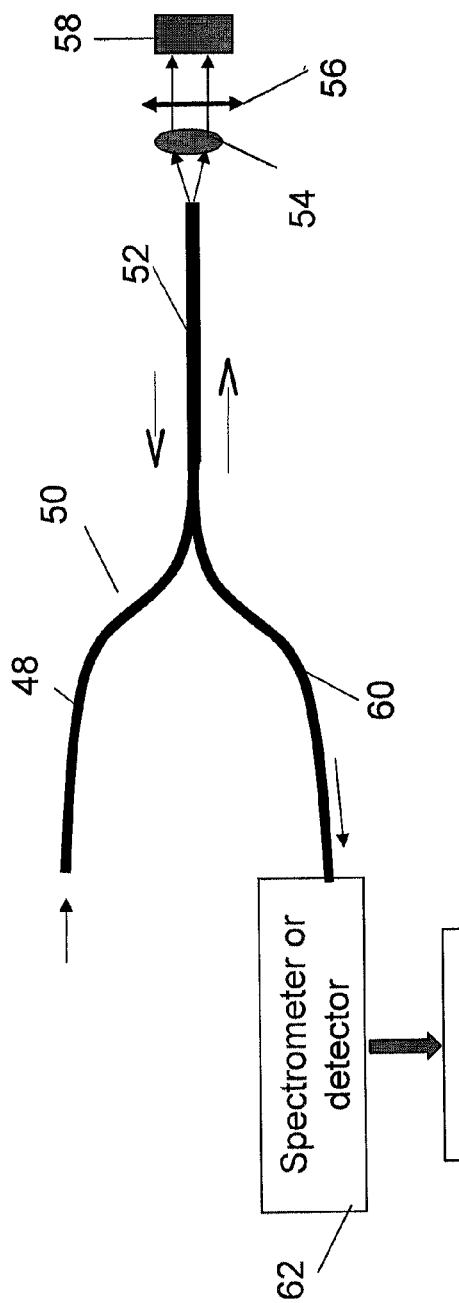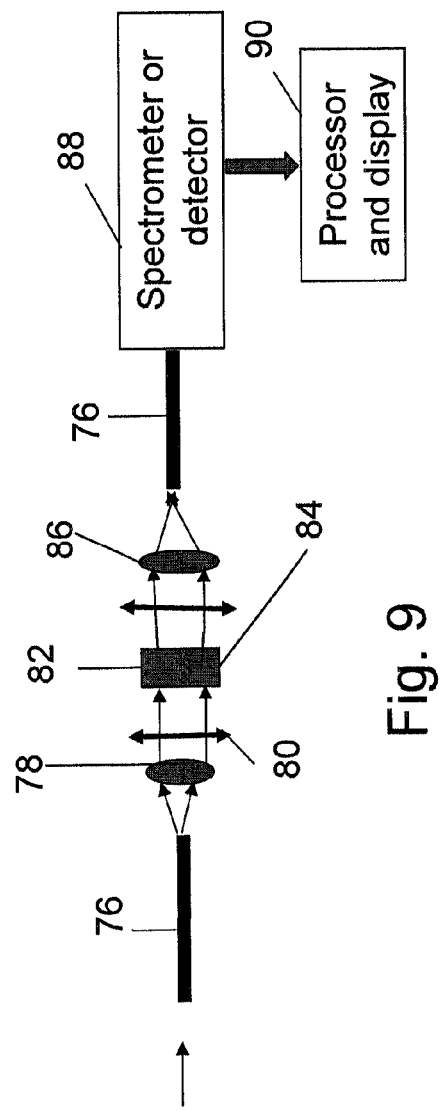

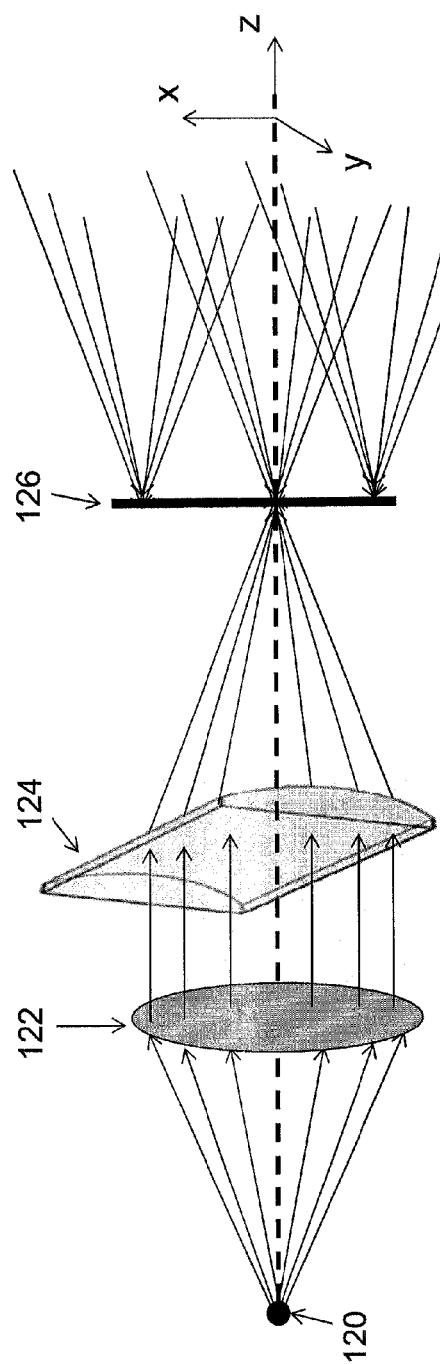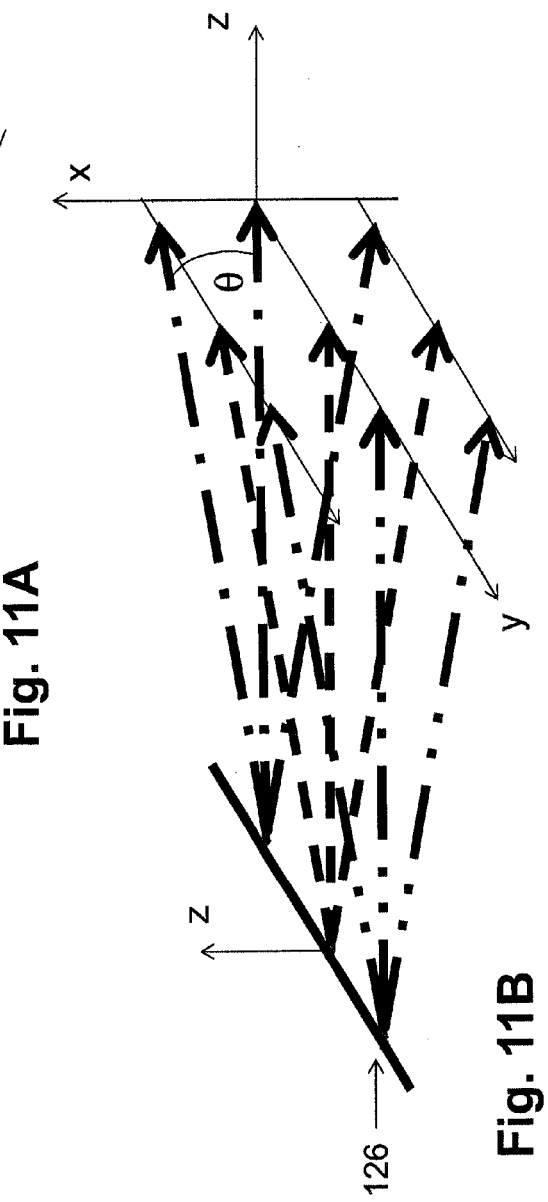
Fig. 11A
Fig. 11B

OPTICAL SENSOR WITH ENHANCED SENSITIVITY

CROSS-REFERENCE TO RELATED APPLICATIONS

This application is the U.S. National Phase of International Application No. of PCT/IL2012/000075, filed Feb. 14, 2012, which claims priority to U.S. Provisional Application No. 61/442,318, filed Feb. 14, 2011, the contents of each are hereby incorporated by reference in their entireties.

FIELD OF THE INVENTION

The invention is from the field of optical biosensing. In particular the invention is from the field of surface plasmon resonance sensing devices that are used as biosensors.

BACKGROUND OF THE INVENTION

Publications and other reference materials referred to herein are numerically referenced in the following text and respectively grouped in the appended Bibliography which immediately precedes the claims.

Surface plasmon resonance (SPR) sensing devices have seen a tremendous awareness during the last decade both from a fundamental point of view and as highly sensitive devices for optical sensing of small biological or chemical entities in gases and liquids. There are two main types of surface plasmons (SPs): extended and localized. The extended SP is considered as more classical since it has been known for longer time. It can be described as a longitudinal electromagnetic wave (EM) in a two dimensional electron gas that exists on the surface of metals. Localized SPs on the other hand have become more familiar only during the last two decades. They are excited in metallic structures with dimensions less than half the wavelength of the exciting EM wave. In both cases the incident EM field has to be polarized in the plane of incidence (transverse magnetic (TM) polarization).

Biosensing is a strongly active field of research [1] due to the need for high sensitivity, rapid, specific and reliable biosensors both for environmental control and for medical diagnosis. Optical biosensors in particular are important for their simplicity, compactness, their potential to allow remote sensing and imaging to read many sensor chips in parallel [2]. Nylander and Liedberg [3] demonstrated high sensitivity sensing in the early 80's using surface plasmon resonance (SPR) phenomenon. Since then, SPR phenomenon based sensing has been receiving continuously growing attention [4]]. In order to improve on the already successful panoply of optical biosensors, nano-photonic structures composed of periodic metallic openings with dimensions less than the wavelength can be used Within the periodic structures, quite unexpected phenomena emerge related to the existence of localized SPR (LSPR) and extended SPR (ESPR) excitations. One of the peculiar phenomena is the enhanced optical transmission (EOT), in which transmittance through such nano openings, exceeds the relative area ratio (geometric limit) as predicted originally by Ebbesen et al. [5]. This result was mismatched with Bethe's aperture theory [6], which predicts negligible transmission through a single small hole in a thin metal film. The phenomenon of enhanced optical transmission is also termed extraordinary optical transmission. EOT causes large sensitivity because it involves two intertwined processes: (1) transmission through the nanoapertures and (2) scattering of evanescent waves by the apertures. Lee et al. [7,8] demonstrated a comparative study which verifies higher sensitivity of nanoslits over nanoholes based structures and therefore nanoslits are better candidates for sensing designs. One of the applications of EOT phenomenon is sensing in a water environment.

By attaching molecules to the nanoslits structure, the transmission is modified significantly and the overall transmission resonance undergoes a large shift in wavelength due to surface plasmons and cavity modes [9,10]. There are several conditions for surface plasmon excitation, which depend on parameters such as angle of incidence, grating geometry, wavelength, and the dielectric constants of the metal and dielectrics below and above the grating. The resonance is observed in terms of a sharp dip in reflection or sharp peak in transmission in the output optical signal at either the resonance angle (angular interrogation) or the resonance wavelength (spectral interrogation). Any change in refractive index near the interface causes a change in the value of the resonance location. This means that the resonance wavelength or incidence angle is sensitive to refractive index variations, a fact that makes this structure a potential sensor. In addition, periodically structured metallic films constituted of sub-wavelength apertures based on SPR phenomenon are potential sensors for a variety of applications including water and food quality control. It remains unclear however, whether this type of sensor is able to detect large biological or biochemical entities with dimensions larger than the slit width. In the food industry in general and in the water industry in particular, the quality of the product is evaluated by chemical (or microbiological) time dependent analysis. These processes include techniques such as chromatography, spectrometry, electrophoresis, etc., which enable recognizing water pollutants of small size and of small amounts. SPR based optical biosensors have gained attention due to their speed of detection, high specificity, high sensitivity and the possibility of on-line real-time analysis [11]. Since the extraordinary transmission of subwavelength grating based SPR sensors is a result of SPR, they are expected to have good surface sensitivity similar to conventional SPR sensors [8,12]. Subwavelength grating based SPR devices show sensitivity of about 400 nm/RIU [10,13] when designed to operate in the visible region of the spectrum.

In the visible range of the spectrum the enhanced local field extends only to a range of about 50-100 nm from the slits; hence the sensor will not sense the whole volume of a bacteria cell for example. This problem is well known in the traditional prism coupled SPR sensors even though extended SP waves have a relatively larger propagation length along the surface of the order of 10 μm [14]. Long range SPR configurations have been proposed [15] to resolve this problem. Sensors based on EOT, strongly depend on the detailed structure of the nanomaterial. It is well known that the aperture size and type of the metallic nanostructures have different contributions in the extraordinary transmission [16,17]. However, according to Lee et al. [8], the width of nanoslits does not affect the sensitivity of the sensor. The present inventor has proposed a methodology for increasing the sensitivity of resonant based structures by maximizing the electromagnetic interaction of the evanescent field with the analyte [18]. This methodology was also confirmed numerically to be valid for SPR sensors [19].

It is a purpose of the present invention to provide SPR sensors that have higher sensitivity to pollutants than structures designed in the visible region.

It is another purpose of the present invention to provide SPR sensors that possess appropriate stability for use in a water environment.

It is another purpose of the present invention to provide SPR sensors that overcomes the problem of detecting large biological entities.

Further purposes and advantages of this invention will appear as the description proceeds.

SUMMARY OF THE INVENTION

In a first aspect the invention is a surface plasmon resonance (SPR) sensor to determine the presence and quantity of biological or chemical entities in an analyte. The sensor of the invention comprises:
- (a) a metal periodic structure deposited as a thin layer of a noble metal, comprising a one dimensional array of nanoslits or a two dimensional array of nanoholes on a transparent dielectric substrate;
- (b) a nm-thick layer of transparent dielectric protection layer on top of the metal periodic structure; and
- (c) a functionalization layer, which acts as a binding layer to biological or chemical entities in an analyte that is in contact with the functionaliztion layer.

The sensor of the invention has the following properties:
- (a) the spaces perforated in the metal are at least partially filled by a material with a refractive index as close as possible to that of the substrate;
- (b) the thickness of the metal layer is no more than 100 nm;
- (c) the refractive index, transparency and the thickness of the dielectric protection nanolayer are chosen so that it does not affect the sensor sensitivity;
- (d) the thickness of the dielectric protection layer is no more than 20 nm; and
- (e) the presence of the material in the spaces perforated in the metal distances the analyte material from the metal-substrate interface, thereby improving the signal to noise ratio for the spectral/angular peak corresponding to the plasmon excited at the metal-substrate interface allowing this spectral peak to be used as a reference relative to which the spectral peaks corresponding to the plasmon excited at the metal-analyte interface is measured.

In embodiments of the sensor of the invention the period of the metal structure is larger than 600 nm.

In embodiments of the sensor of the invention the material that at least partially fills the spaces perforated in the metal have the same thermooptic coefficient as the analyte.

In embodiments of the sensor of the invention the difference between the refractive index of the substrate and analyte is at least 0.1.

In embodiments of the sensor of the invention an anti-reflection coating is added on the external surface of the substrate.

Embodiments of the sensor of the invention comprise dielectric spacers that hold a transparent glass plate parallel to the protection layer with a gap having less than 200 microns thickness between the glass plate and the protection layer. The gap forms a channel through which a liquid analyte can be contained or flow. These embodiments may comprise at least one of:
- (a) antireflection coatings covering the transparent glass plate; and
- (b) a transparent electrode coated on the side of the transparent glass plate facing the analyte, thereby allowing an electric field to be applied between the metal periodic structure and the top glass plate.

In a second aspect the invention is an array comprised of a plurality of sensors of the first aspect. Each of the sensors in the array is constructed on a common substrate and each of the sensors has dimensions equal to at least twenty times the period of the spacing between the adjacent nanoslits or the distance between adjacent nanoholes.

In embodiments of the array of the invention the functionalization layer of at least one of the sensors can be different from the functionalization layer of other sensors in the array so that each sensor can monitor different biological or chemical entities.

In embodiments of the array of the invention the period in each sensor or group of sensors in the array can be different from the period of other sensors or group of sensors in the array so that each sensor or group of sensors will be monitored with slightly different spectral or angular range.

In embodiments of the array of the invention the sensor plane can be imaged on a camera and the wavelength can be controlled by a tunable source, using a tunable filter or monchromator.

In a third aspect the invention is methods of using the sensor of the first aspect or the array of the second aspect to determine the presence and quantity of biological or chemical entities in an analyte.

An embodiment of the method of the invention comprises:
- (a) providing an optical setup adapted to irradiate an analyte covered sensor of claim 1 with TM polarized light;
- (b) measuring the resonance wavelength or incidence angle of the resonant transmission peaks or reflection dips of the plasmon excited at the metal-analyte interface relative to the resonance wavelength or incidence angle of the resonant transmission peaks or reflection dips of the plasmon excited at the metal-substrate interface.

An embodiment of the method of the invention comprises:
- (a) providing an optical setup adapted to irradiate an analyte covered sensor of claim 1 with an input beam polarized at 45 degrees to the plane of incidence;
- (b) passing the output beam through either a crossed or a parallel polarizer;
- (c) measuring the phase retardation between TE and TM waves of the plasmon excited at the metal-analyte interface that are incident on the sensor relative to the phase retardation between TE and TM waves of the plasmon excited at the metal-substrate interface that are incident on the sensor.

An embodiment of the method of the invention comprises:
- (a) providing an optical setup adapted to irradiate an analyte covered sensor of claim 1 with an input beam polarized at 45 degrees to the plane of incidence;
- (b) passing the output beam through either a rotating polarizer, or through a polarization rotator followed by a fixed polarizer, or through a phase modulator followed by a fixed polarizer.
- (c) extracting the polarimetric or ellipsometric properties of the transmitted or reflected beams corresponding to the resonance wavelengths or angles of the plasmon excited at the metal-analyte interface relative to the ellipsometric or polarimetric properties of the same beams corresponding to resonance wavelengths or angles of the plasmon excited at the metal-substrate interface.

In this embodiment the polarimetric or ellipsometric properties of the transmitted or reflected beams are extracted from a minimum of three measurements corresponding to three positions of the output polarizer or the polarization modulator.

An embodiment of the method of the invention comprises:
(a) providing an optical setup adapted to:
  (i) irradiate an analyte covered sensor of claim 1 with an incoming beam of light that has passed through an input polarizer oriented to the TM orientation, wherein the input beam is a single wavelength diverging beam with few degrees divergence; and
  (ii) to direct the output beam that passes through or is reflected from the analyte covered sensor to a detector array or a camera; and
(b) measuring on the output of the detector array or camera a dark line on a bright background in the reflected beam or a bright line on a dark background in the transmitted beam corresponding to the plasmon excited at the metal analyte interface relative to a dark line on a bright background in the reflected beam or a bright line on a dark background in the transmitted beam corresponding to the plasmon excited at the metal substrate interface.

All the above and other characteristics and advantages of the invention will be further understood through the following illustrative and non-limitative description of embodiments thereof, with reference to the appended drawings.

BRIEF DESCRIPTION OF THE DRAWINGS

FIG. 8 schematically shows a fiber optic based system for making SPR measurements in reflection using a 2×1 fiber coupler and the sensor shown in FIG. 1;

FIG. 9 symbolically shows a transmission type fiber optic based setup that uses the sensor described in FIG. 1;

FIG. 11A and FIG. 11B schematically show an embodiment of the angular mode of operation in which the diverging beam is mainly diverging in the plane of incidence;

DETAILED DESCRIPTION OF EMBODIMENTS OF THE INVENTION

The invention is a structure for a surface plasmon resonance (SPR) sensing device to determine the presence and quantity of biological or chemical entities in an analyte that is designed for the infrared. The invention also is a method of using the sensor of the invention to improve the detection limit by using the peak corresponding to the plasmon excited at the metal-substrate interface as a reference. In addition the invention is cavity type design for the sensor that is suitable for sensing of fluid samples. Another aspect of the invention are systems that incorporate the sensor of the invention that are adapted to allow angular mode of measurement at single wavelength, spectropolarimetric measurements, multisensors imaging and fiber based configurations.

The structure of the SPR sensor of the invention enhances the sensitivity of prior art SPR sensors and overcomes the problem of detecting large biological entities by extending the penetration depth of the electromagnetic field inside the analyte. The SPR sensor of the invention exhibits higher sensitivity to pollutants than structures designed in the visible region, stability in water environments, and suitability for detection of large biological entities.

The improved sensitivity of the SPR sensor of the invention over that of prior art sensors is achieved by providing a metal periodic structure with period larger than 600 nm and metal thickness less than 100 nm. The metal is deposited as a thin layer of a noble metal, e.g. gold or silver, comprising a one dimensional array of nanoslits or a two dimensional array of nanoholes on a transparent dielectric substrate and covered on top with nm-thick layer of transparent dielectric. The spaces perforated in the metal are partially filled by a material with similar properties to those of the substrate and preferably having the same thermooptic coefficient as the analyte. The difference in the refractive index of the substrate and analyte should be at least 0.1.

Figure 1:
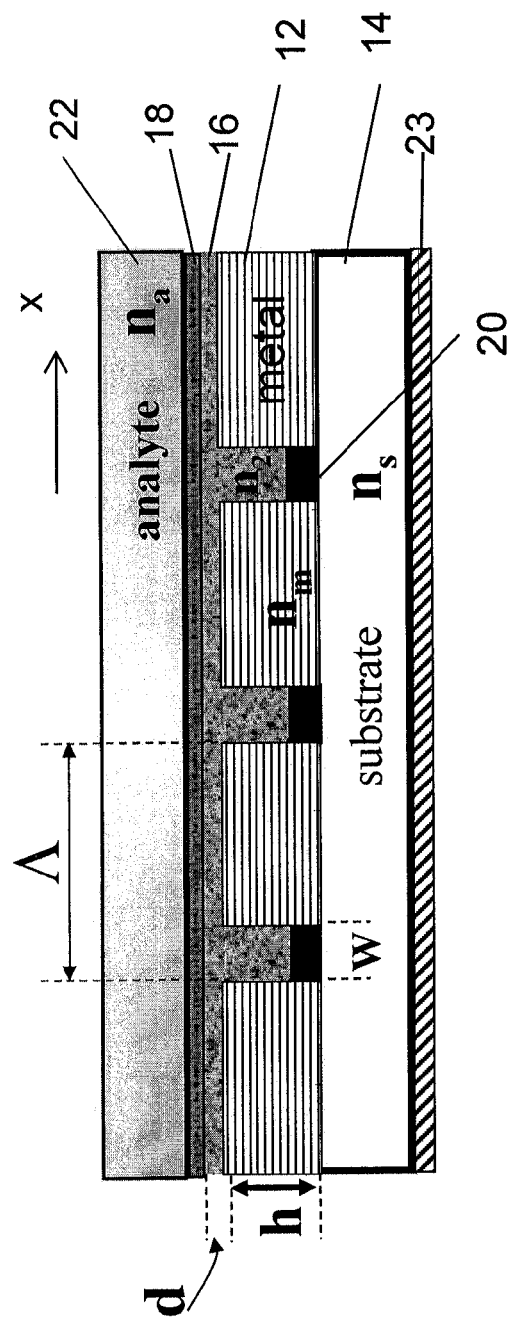
FIG. 1 schematically is a cross-sectional view showing the general structure and the geometrical parameters of a part of a sensor of the invention.

The invention will now be described for the case of a one dimensional (1D) periodic array of nanoslits, although the invention applies to other periodic structures in metals such as a 2D array of nanoholes. FIG. 1 is a cross-sectional view showing an analyte layer covering a part of sensor (10) of the invention showing the general structure and the geometrical parameters. Seen in the figure is an array of metallic nanoslits (12) that has been created as a metallic film on a transparent substrate (14). For certain metals and substrates such as gold on glass an additional adhesion layer of few nm thick Ti or Cr underneath the gold will be deposited to improve the stability of the gold layer. The array (12) is covered with a protection nanolayer (16). The protection layer exists mainly for protecting the metal surface from oxidation. This is particularly important for silver and almost not important for gold. The refractive index, transparency and thickness of protection nanolayer (16) are chosen so that it does not affect the sensor sensitivity and in certain cases might improve it. On top of nanolayer (16) is located a functionalization layer (18) which acts as a binding layer to the biological or biochemical entities in the analyte (22). At least a part of the slits in the metal structure are filled with material (20), which has similar properties as the substrate. The function of material (20) is to distance the analyte material from the metal-substrate interface, thereby improving the signal to noise ratio for the spectral peak corresponding to the plasmon excited at this interface.

In embodiments of the structure shown in FIG. 1 some or all of the following conditions are met:
(a) material (20) has a refractive index as close as possible to that of the substrate (14);
(b) the refractive index of substrate (14) differs from that of analyte (22) by at least 0.1;
(c) the thermooptic coefficient of substrate (14) is as close as possible to that of analyte (22);
(d) the thickness of the dielectric layer (16) is 20 nm or less; and
(e) an anti-reflection coating (23) is added on the external surface of the substrate to minimize reflections and spurious oscillations in the reflection spectrum which can affect the precision of finding the resonance location.

Optimum results are obtained when all of these conditions are met.

The geometrical parameters shown in FIG. 1 are: The height (thickness) of the metal layer 'h', the distance between adjacent metal strips=the width of a nanoslit 'w', the thickness of the protection nanolayer 'd', and the pitch (period) of the nanoslit structure 'Λ'. The indices of refraction of the materials of the substrate, metal, protective layer, and analyte are respectively represented by '$n_s$', '$n_m$', '$n_2$', and '$n_a$'.

Figure 2B:
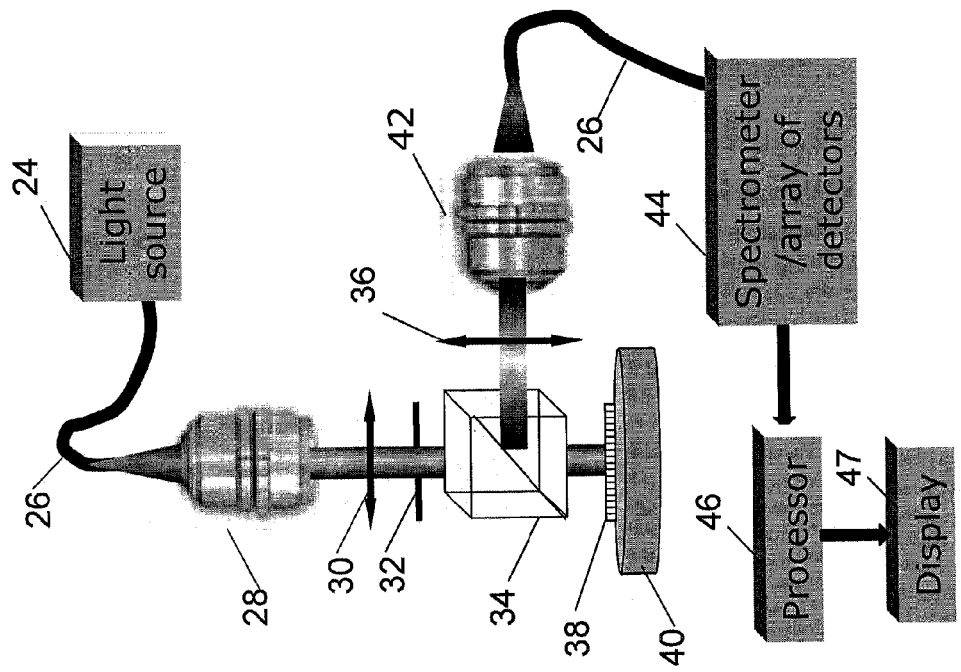
FIGS. 2A and 2B schematically show systems for making SPR measurements in transmission and reflection respectively at normal incidence using the sensor shown in FIG. 1.
Figure 2A:
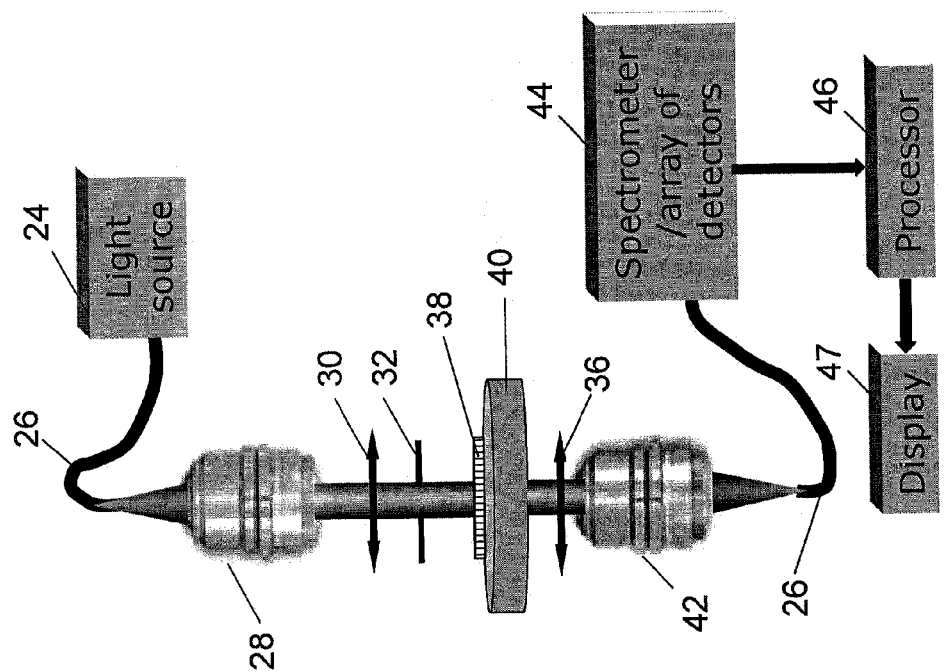

FIGS. 2A and 2B schematically show embodiments of systems for making SPR measurements in transmission and reflection respectively at normal incidence using the sensor shown in FIG. 1. Light from the light source (24) is conducted by optical fiber (26) to lens system (28) where the light beam is expanded and collimated. The beam of light then passes through polarizer (30) and aperture (32). It should be understood that in principle oblique incidence of light is also possible and FIGS. 2A and 2B are given for illustration and should not be understood as a limitation.

In the transmission setup (FIG. 2A) the polarized light is incident directly on the sample (38), which is composed of an analyte layer (22) and sensor (10) of the invention mounted on rotation stage (40), which is used to orient the polarized light with respect to the metallic nanoslits of the sensor. The portion of the light that passes through sample (38) passes through an analyzer (36), a lens system (42), and an optical fiber (26) to a spectrometer (or array of detectors) (44). The output of spectrometer (44) is conducted to a processor unit (46), e.g. a PC, where it is analyzed and displayed on a display (47). The transmission spectrum will show a peak at the EOT. The location of the peak is a measure of the variations in the refractive index of the analyte.

In the reflection setup (FIG. 2B) the polarized light passes through beam splitter (34). The light transmitted through the beam splitter is incident directly on the sample (38) and is reflected back to the beam splitter, where it is directed through an analyzer (36), a lens system (42), and an optical fiber (26) to a spectrometer (or array of detectors) (44). The output of spectrometer (44) is conducted to a processor unit, e.g. a PC, where it is analyzed and displayed. The reflected spectrum will show a dip at the EOT. The location of the dip is a measure of the variations in the refractive index of the analyte.

Figure 7:
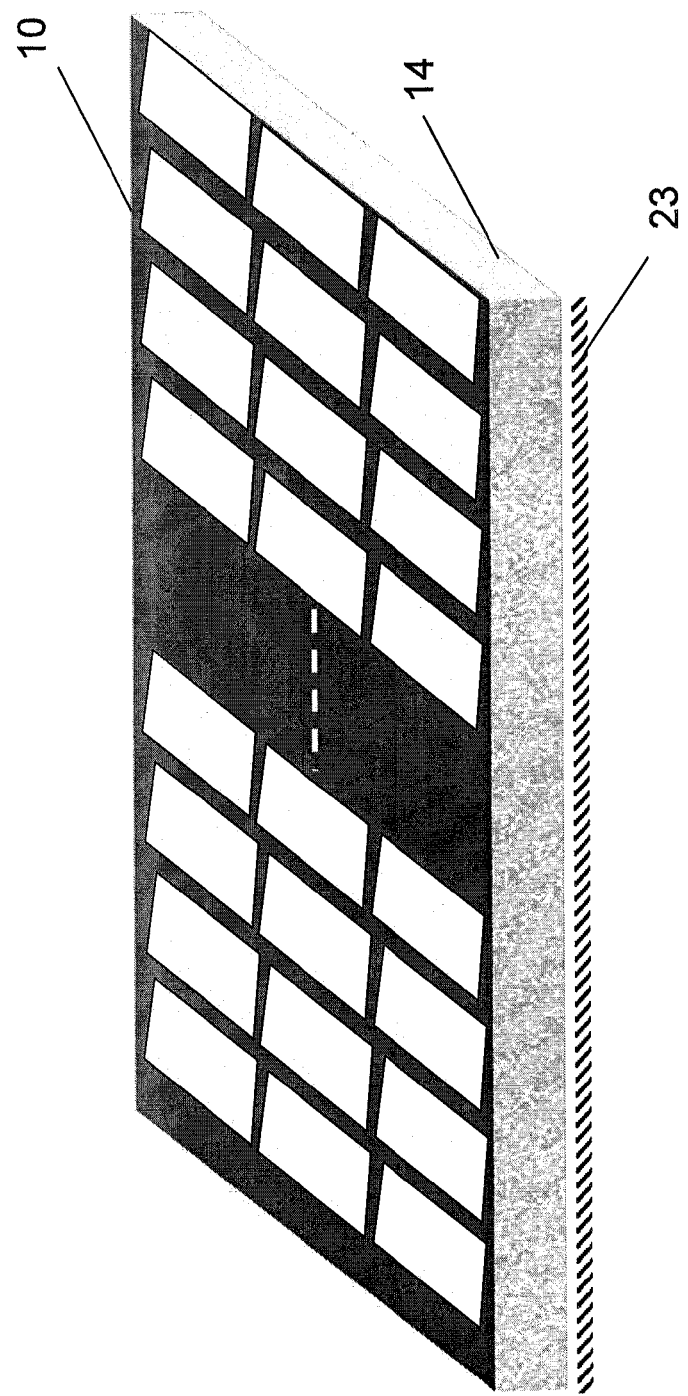
FIG. 7 symbolically shows an embodiment of the invention comprising a plurality of sensors of the invention constructed as an array on a common substrate.

In the setups shown in FIG. 2A and FIG. 2B the detector can be an imaging detector such as a CCD camera connected to a computer that monitors the output of each single pixel of multiple sensing elements such as the one shown in FIG. 7 separately. For this imaging configuration, the sensor plane is imaged on a CCD or CMOS camera plane and the wavelength contents are synthesized either using a tunable filter, a monchromator or using the color synthesis capability of the camera. The tunable source or tunable filter will be synchronized with the detector in order to read the spectrum of a pixel independently.

Figure 3:
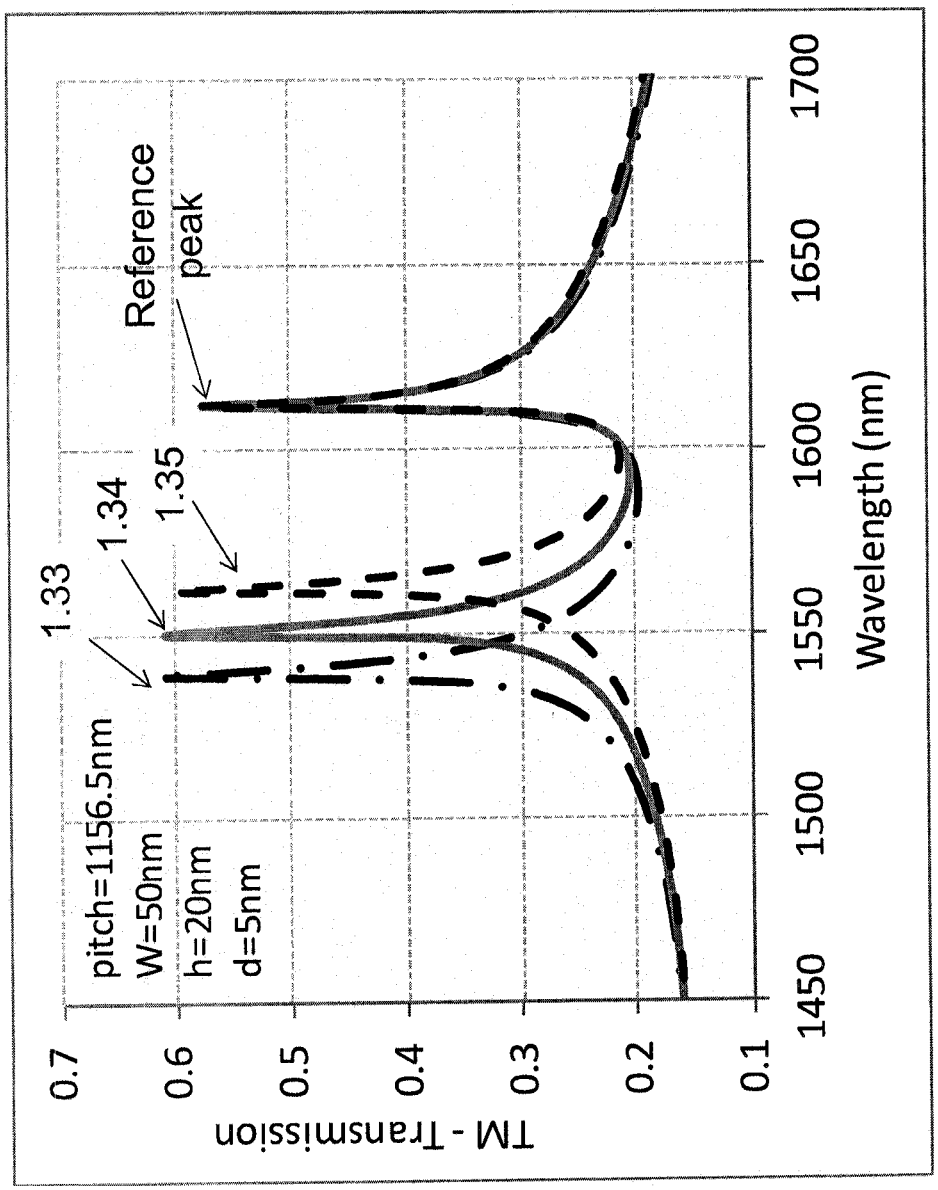
FIG. 3 shows calculated transmission results vs. wavelength at normal incidence for analytes having three different indices of refraction in the infrared through the structure shown in FIG. 1.

When the nanoslit structure is irradiated by TM polarized light at normal incidence for example using the setup in FIG. 2A, resonant transmission peaks as shown in FIG. 3 are obtained. FIG. 3 shows calculated transmission vs. wavelength results for analytes having three different indices of refraction in the infrared through the structure shown in FIG. 1. The calculations were performed using a commercially available software (GSOLVER) based on the rigorous coupled wave approach for solving Maxwell's equations in periodic structures. The parameters of the structure are: Λ=1156.5 nm, W=50 nm, h=20 nm, and d=5 nm. The metal is silver coated with a PMMA protection layer on silica glass substrate. The spaces in the grating are also filled with PMMA. The analyte is water and the calculation is for three analyte indices showing sensitivity of nearly 1200 nm/RIU. The curve composed of alternating dots and dashes is for n 1.33, the solid curve is for n=1.34, and the dashed curve is for n=1.35. Each of the curves is comprised of two peaks—the one at the left is from the plasmon excited at the analyte-metal interface and the peak at around 1620 nm is from the plasmon excited at the substrate-metal interface.

From Maxwell's equations it is know that the surface Plasmon wave excited at the metal dielectric interface has the wave number:

$$k_{SP} = \left\{ k_0 \sqrt{\frac{\varepsilon_m \varepsilon_a}{\varepsilon_m + \varepsilon_a}} \right\}$$

with $k_0=2\pi/\lambda$ being the wavenumber of incident light. The resonance wavelength is found from the k vector, i.e. wavenumber, matching condition of SPR existence. At normal incidence the wavenumber along the surface (x direction) is provided by the grating: $k_x=2\pi/\Lambda$ which needs to be equal to the real part of $k_{SP}$ in order to excite the SP wave, thus giving the condition $$\lambda_{SP} \approx Re\left\{ \Lambda \sqrt{\frac{\varepsilon_{mr} \varepsilon_a}{\varepsilon_{mr} + \varepsilon_a}} \right\} \quad (1)$$

where the x direction is parallel to the substrate-metal or analyte-metal interfaces along the gratings wave vector, $\in_{mr}$ is the real part of the metal dielectric constant and $\in_a$ is the dielectric constant of the analyte. The sensitivity S of the sensor is measured in nm per refractive index units (nm/RIU) defined as the slope of the variation of the resonance wavelength with the analyte index $n_a=\sqrt{\in_a}$ and can be derived from equation (1) as:

$$S = \frac{\partial \lambda_{SP}}{\partial n_a} = \frac{\lambda_{SP}}{\sqrt{\varepsilon_a}} \frac{\varepsilon_{mr}}{\varepsilon_{mr} + \varepsilon_a - 0.5\varepsilon_{mr}^{-1}\varepsilon_a \lambda_{SP} \frac{\partial \varepsilon_{mr}}{\partial \lambda}} \quad (2)$$

Hence the sensitivity scales linearly with the structure period which for the IR requires a period larger than 700 nm as was shown by the group of the present inventor recently [20]. However the inventor has found that it is possible to obtain resonances in the IR using periods less than 700 nm by using thicker metallic gratings. These resonances are based on cavity type resonances and do not follow equations (1) and (2); however they exhibit high sensitivity to the analyte refractive index and their sensitivity also scales with the wavelength.

Another important factor affecting the sensitivity is the penetration depth of the electromagnetic field inside the analyte which can be estimated from the following equation:

$$\delta_a = \frac{\lambda}{2\pi} \cdot \sqrt{\frac{\varepsilon_a + \varepsilon_{mr}}{-\varepsilon_a^2}} \quad (3)$$

For example for silver at $\lambda=1500$ nm $\varepsilon_{mr}=-115.5$, which is much larger than $\varepsilon_a=1.769$, thus giving a penetration depth of about $\delta_a=0.96\lambda \approx 1.44$ µm. For the visible range $\lambda=600$ nm on the other hand $\varepsilon_{mr}=-14.14$, thus giving $\delta_a=0.316\lambda \approx 0.19$ µm. Hence the penetration depth in the near IR (NIR) range is larger by a factor of 8 than that in the visible range, although the wavelength ratio is only 2.5.

The propagation length $L_x$ of the SP along the surface of the metal at the interface with the analyte can be estimated from:

$$L_x = \frac{\lambda}{2\pi} \cdot \frac{\varepsilon_{mr}^2}{\varepsilon_{mi}} \cdot \left[\frac{\varepsilon_a + \varepsilon_{mr}}{\varepsilon_a \cdot \varepsilon_{mr}}\right]^{3/2} \quad (4)$$

The imaginary part of silver dielectric constant at 1500 nm is $\varepsilon_{mi}=12.3$ and hence $L_x \approx 72\lambda \approx 108$ µm. For the visible ($\lambda=600$ nm) on the other hand $\varepsilon_{mi}=0.96$ giving $L_x \approx 11.5\lambda \approx 6.9$ µm. Hence the plasmons in the IR travel a longer range along the interface, an important fact for enhancing the sensitivity and improving the detection limit because then the resonance peak becomes narrow.

According to the invention, the transmission/reflection peaks of the plasmon excited at the metal-analyte interface is measured relative to the fixed resonant peak shown in FIG. 3 at a wavelength of around 1620 nm. This peak corresponds to a plasmon excited at the metal-substrate interface and therefore it is insensitive to the analyte refractive index. The fact that this peak corresponds to a surface plasmon excited at the metal-substrate interface was investigated thoroughly by the research group [21,22,23] of the inventor of the present invention by showing that its position varies with the substrate refractive index according to equation 1 by simply replacing $\varepsilon_a$ by the dielectric constant of the substrate $\varepsilon_s$. Since temperature and other system drift noise effects affect the transmission/reflection peaks of the plasmon excited at the metal-analyte interface and that excited at the metal-substrate interface in the same manner, measurement of the transmission/reflection peaks of the plasmon excited at the metal-analyte interface relative to the fixed resonant peak neutralizes the influence of stability problems of the setup such as temperature variations, mechanical vibrations and misalignments.

Figure 4:
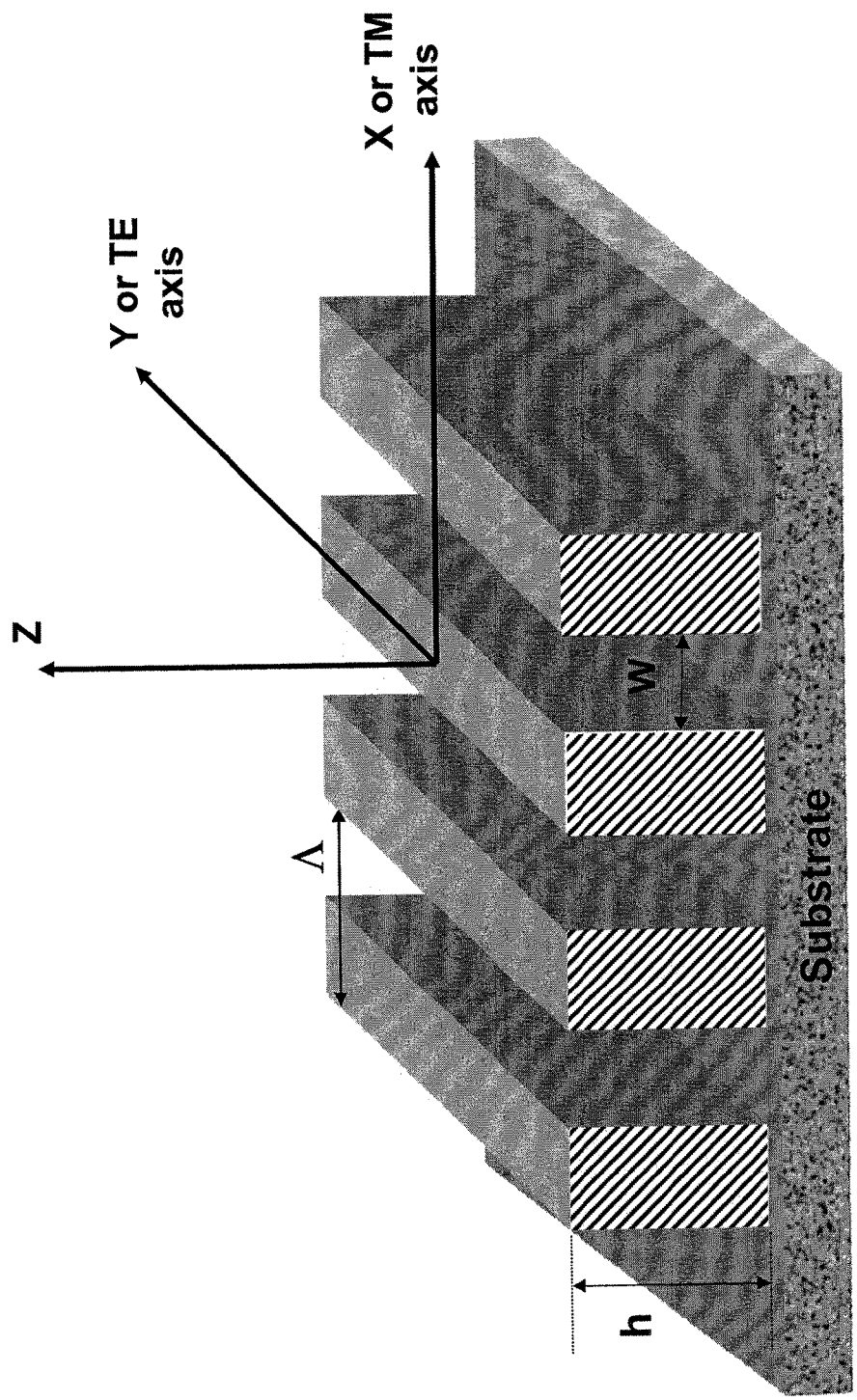
FIG. 4 schematically shows the grating structure and the direction of the TE and TM axes.

Another method of using the sensor of the invention is based on the use of the phase retardation between the TE and TM waves incident on the sensor. FIG. 4 schematically shows the grating structure and the direction of the TE and TM axes. Near the EOT resonance there is a phase jump of the TM wave. Since there is no EOT resonance for the TE polarization, the TE wave experiences very little phase change. As a result phase retardation between the two orthogonal polarizations arises causing a change in the polarization state.

Phase variations can be measured with an interferometer however the inventor proposes using a common path type interferometer based on the polarization change due to the different phase accumulations of two orthogonally polarized waves.

The best preferable embodiment for the phase mode is to have the incident linear polarization oriented at 45 degrees with respect to the slits direction in order to excite both the TE and the TM waves. Upon transmission or reflection the two waves will be recombined using another output polarizer (analyzer) in crossed position to the first polarizer. If the amplitudes of the TE and TM waves are similar, the signal will be proportional to $\sin^2(\Gamma/2)$ where $\Gamma = \phi_{TM} - \phi_{TE}$ is the accumulated phase retardation in reflection or transmission between the TM and TE waves. When the input and output polarizers are parallel to each other the signal will be proportional to $\cos^2(\Gamma/2)$, which is thus another option for aligning the polarizers. However the crossed polarizers case is preferable because with this configuration some unwanted back reflections can be extinguished because the output polarizer is crossed to the incident polarizer.

Because the amplitudes of the TM and TE waves are different upon reflection/transmission the output polarization will be in general elliptical. Therefore determination of the parameters of the polarization ellipse provides another way of measuring signals that are sensitive to the refractive index variations of the analyte. Conventional techniques of ellipsometry or polarimetry known in the art and particularly applied to surface plasmon resonance in the Kretschmann configuration can be used such as the rotating polarization modulation technique [24] or the phase modulation technique [25].

Figure 5:
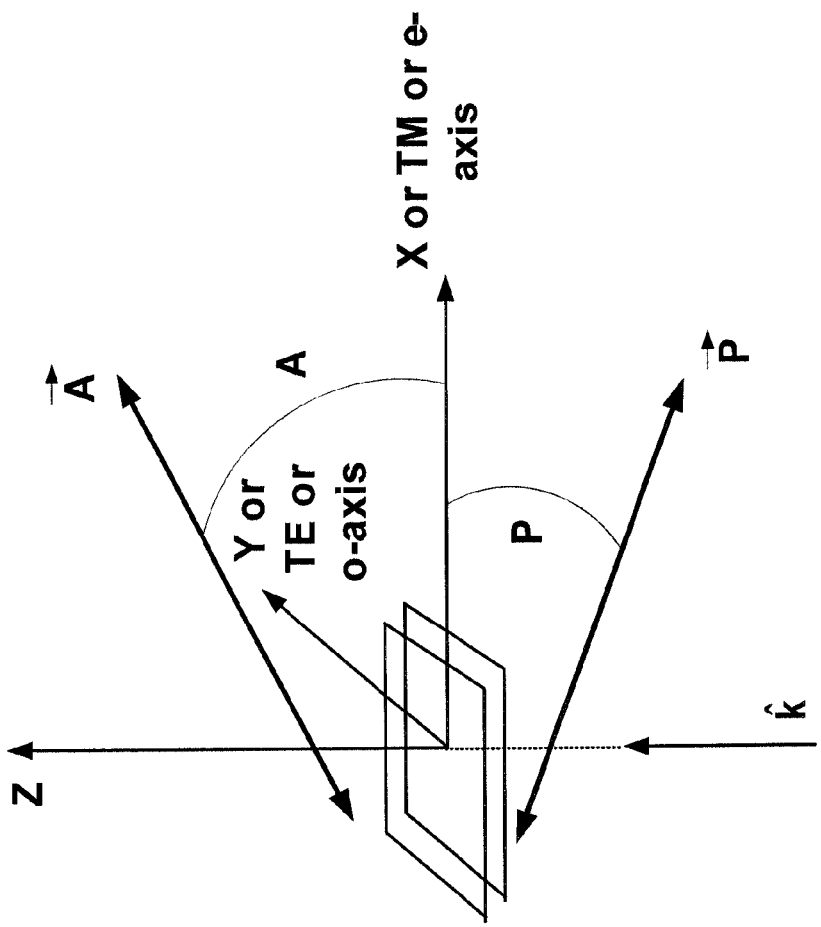
FIG. 5 schematically shows the polarizer and analyzer orientations and similarity of the perforated metal film to an anisotropic plate with two eigen-axis.

In a method of the invention a three point technique is used to extract the polarization ellipse parameters. The perforated metal plate can be described in good approximation for this purpose as an anisotropic plate with two axis 'o' and 'e' (to designate the TE and TM axis for example). FIG. 5 schematically shows the polarizer and analyzer orientations and the similarity of the perforated metal film to an isotropic plate with two eigen-axes.

In general the polarizer and analyzer axes can be oriented at arbitrary azimuthal angles P and A with respect to the optical axis, e.g. the direction of the slits; however, for the best embodiment, P=45 degrees. In this case the detector signal can be written as:

$$I = I_m [|\cos^2 A \tan \psi \exp(i\Gamma) + 0.5 \sin 2A|^2 + |0.5 \sin 2A \tan \psi \exp(i\Gamma) + \sin^2 A|^2] \quad (5)$$

where $I_m$, represents the signal coming from the source and other reflection/absorption effects of the optical sample. The angle $$\psi = \arctan\left|\frac{a_{TM}}{a_{TE}}\right|,$$

together with the retardation $\Gamma$, define the polarization state arriving at the detector, where $a_{TM}$ and $a_{TE}$ represent the complex amplitudes for the light eigen-polarizations along the e-axis (TM) and the o-axis (TE) respectively. It is to be understood, however, that the measurements according to the methods of the present invention, are not meant to be limited to the use of the ψ and Γ parameters, but could equally be performed in terms of the more conventionally used ellipticity and azimuth of the polarization ellipse.

In order to determine ψ, and Γ, at least three measurements must be made, such as can be achieved by choosing three different polarizer-analyzer orientations. A preferable configuration is obtained when the analyzer is oriented at the three different orientations:

$$A = -\frac{\pi}{4}, 0 \text{ and } \frac{\pi}{4}.$$

The signals then obtained are:

$$I_{ps} = I\left(A = -\frac{\pi}{4}\right) = 0.5I_m\{1 + \tan^2\psi - 2\tan\psi\cos\Gamma\} \quad (7)$$

$$I_{45} = I(A = 0) = I_m\tan^2\psi \quad (8)$$

$$I_{pp} = I\left(A = \frac{\pi}{4}\right) = 0.5I_m\{1 + \tan^2\psi + 2\tan\psi\cos\Gamma\} \quad (9)$$

These equations can be solved to yield the following expressions for ψ, and Γ:

$$\tan\psi = \sqrt{\frac{I_{45}}{I_{pp} + I_{ps} - I_{45}}} \quad (10)$$

$$\cos\Gamma = \frac{\tan\psi}{2} \frac{I_{pp} - I_{ps}}{I_{45}} \quad (11)$$

The angles Γ and ψ as a function of the wavelength or incidence angle contain the necessary information about the anisotropy, the refractive indices dispersions and the layer thicknesses. Note that in equations (10) and (11) ratios between the different intensities appear, hence the insensitivity to the source intensity fluctuations. This way a more accurate measurement and better limit of detection are obtained. The polarization angles can be controlled manually or electronically. It should be understood that that any other ellipsometric technique known in the art can be applied and the invention is not limited to the technique proposed here.

Figure 6:
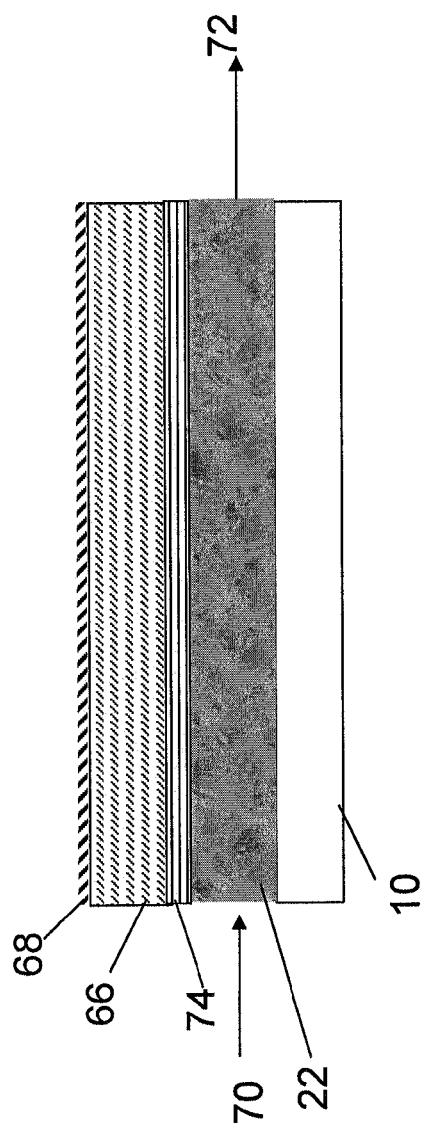
FIG. 6 schematically shows a sampling cell comprising a sensor of the invention and a channel through which a liquid analyte, such as water can be contained or flow.

FIG. 6 schematically shows a sampling cell comprising a sensor of the invention and a channel through which a liquid analyte, such as water can be contained or flow. A sensor (10) having a nanostructure similar to that shown in FIG. 1 is covered with a transparent glass plate (66). Dielectric spacers (not shown in the figure) hold sensor (10) and plate (66) parallel with a gap having less than 200 microns thickness between them. The analyte to be sensed fills this gap and might be flowing by capillary forces or with the help of a micro-pump. The top transparent glass plate (66) is covered with antireflection coatings (68) to minimize interface reflections.

In embodiments of the sampling cell shown in FIG. 6 the top glass plate (66) is coated on the side facing the analyte (22) with a transparent electrode (74) such as indium tin oxide in order to apply an electric field between the perforated metal and the top glass plate for the purpose of dragging the molecules or the entities to be sensed closer to the metal surface. This will increase the speed of the sensor, crucial for certain applications such as for sensing bacteria in water in a short time.

In an embodiment of the invention that is symbolically shown in FIG. 7, a plurality of sensors (10) is constructed as an array on a common substrate (14). Each of the sensors in the array has the structure shown in FIG. 1 but they may have different functionalization layers to attract different molecules or entities in the analyte. In embodiments of the array the period in each sensor or group of sensors in the array is different from the period of other sensors or group of sensors in the array so that each sensor or group of sensors will be monitored with slightly different spectral or angular range. To insure sufficient sensitivity, each of sensors (10) should have dimensions equal to at least twenty times the period (Λ). Antireflection coatings (23) are applied to the bottom side of substrate (14) in order to increase the precision of the measurements.

Herein above three detection methods based on the use of the sensor of the invention have been described. These methods involve: (i) measuring the resonance wavelength or incidence angle of the resonant transmission or reflection peaks; (ii) measuring the phase retardation between TE and TM waves that are incident on the sensor; and (iii) determining the polarization ellipse parameters of the output polarization. In all three methods two results are obtained—the first for the plasmon excited at the metal-substrate interface and the second for the plasmon excited at the metal-analyte interface. The structure of the sensor of the invention insures that the result for the metal-substrate interface is insensitive to the refractive index of the analyte. Therefore this result is used as a reference relative to which all other measurements are made.

In addition to the setup shown in FIGS. 2A and 2B, the detection methods can be carried out in many different ways. A small number of examples will be described herein below. Persons skilled in the art will be able to propose many other optical arrangements into which the sensor of the invention can be incorporated.

Another embodiment of a setup is the fiber optic based setup shown in FIG. 8. This setup uses a 2×1 fiber coupler (50). Light from a broadband or tunable light source enters through fiber channel (48), passes through fiber channel 52 to collimating lens system (54) and polarizer (56), which is oriented for TM polarization. The polarized light is incident upon a sample (58) composed of sensor (10) and an analyte layer (22) as shown in FIG. 1. Light reflected from sample (58) passes through fiber channel (52) and a third fiber channel (60) which is coupled to a spectrometer or a detector array (62). If the fiber coupler is made of polarization maintaining fibers with their axis oriented for TM polarization, then it is not necessary to include polarizer (56) in the setup shown in FIG. 8.

FIG. 9 symbolically shows a transmission type fiber optic based setup that uses the sensor of the invention. Light from a broadband or tunable light source enters the setup through optical fiber (76). The light output from optical fiber (76) is collimated with a lens (78) and passes through a polarizer (80) with its axis oriented in TM direction. The polarized light is incident upon a sample (82) composed of sensor (10) and an analyte layer (22) as shown in FIG. 1 or a flow cell as shown in FIG. 6. The transmitted light is coupled to an output optical fiber (76) by means of a focusing lens (86) and is detected with a spectrometer or a detectors array (88) the output of which is transferred to a processor and display unit (90).

Embodiments of the fiber optic setup of FIG. 9 can have the input polarizer (80) oriented at 45 degrees to the TM direction and an additional output polarizer before the focusing lens (86) oriented either parallel or perpendicular to the first polarizer. If the additional output polarizer located before the focusing lens is rotatable the setup can be used to extract the ellipso-polarimetric properties of the output beam. In another embodiment of a setup used to extract the ellipso-polarimetric properties of the output beam the additional output polarization modulator is followed by a fixed polarizer before the focusing lens.

When the incidence angle is different from zero (oblique incidence) it is well known that the SP waves are excited when the following condition is satisfied:

$$n_a k_0 \sin \theta_i \pm mG = Re\{k_{sp}\} \quad (12)$$

Where $\theta_i$ is the incidence angle, $n_a$ is the analyte index on top of the gratings and $G=2\pi/\Lambda$ is the grating vector characterized by the grating period $\Lambda$. The number m is an integer representing the Fourier harmonic of the electromagnetic field in the gratings region where usually m=1 is the highest and most important. Hence at fixed wavelength the incidence angles can be scanned to obtain the EOT peaks at certain angles satisfying equation (12). An aspect of the present invention is a diverging beam approach that allows the resonance to be detected more accurately and allows multiple sensing.

Figure 10B:
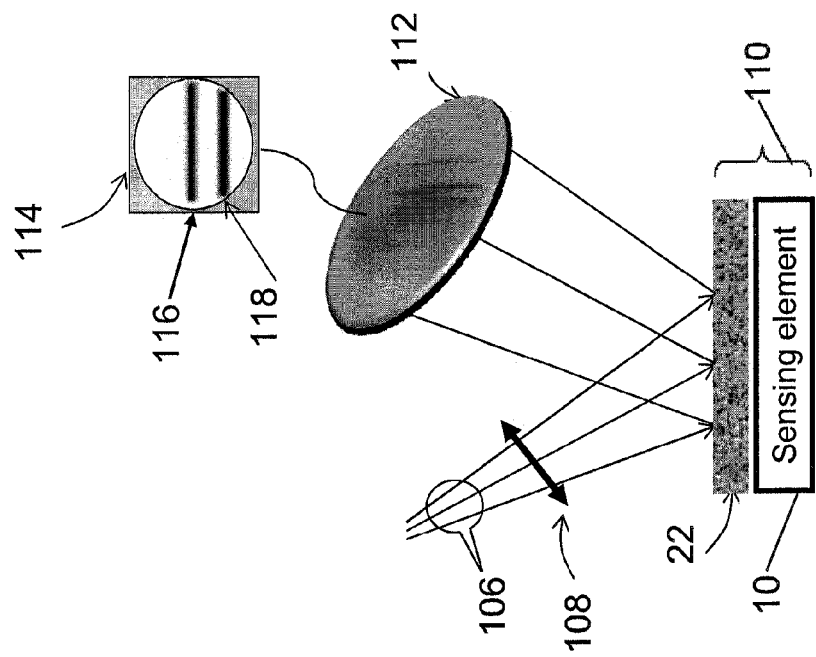
FIG. 10A and FIG. 10B schematically illustrate optical setups for an angular mode of operation of the sensor of the invention in transmission and reflection respectively.
Figure 10A:
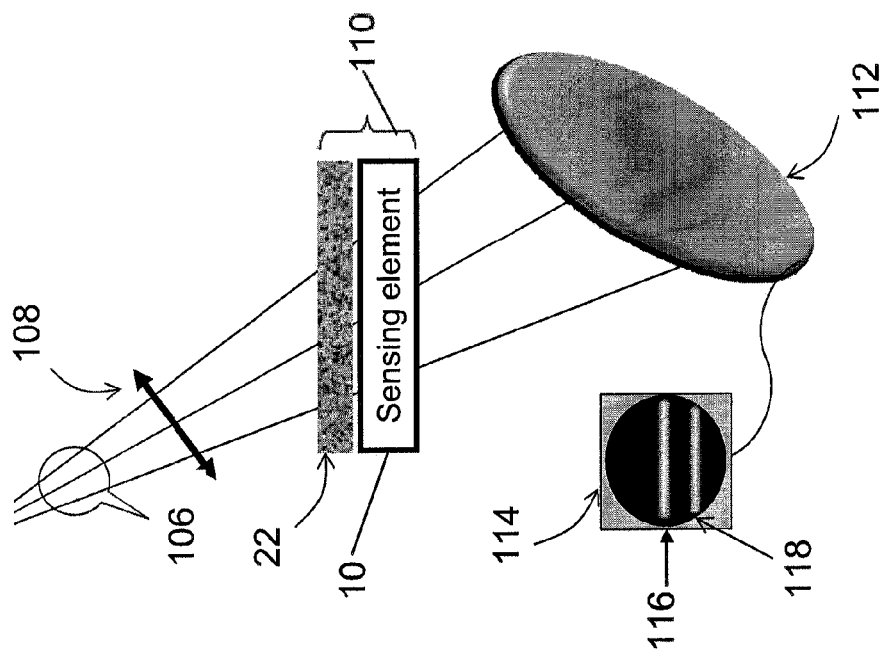

FIG. 10A and FIG. 10B schematically illustrate optical setups for an angular mode of operation of the sensor of the invention in transmission and reflection respectively. In these setups a single wavelength is used corresponding to the nominal resonance location at the angle corresponding to the center of the beam. On the way to sample (110) the incident beam (106) diverges with few degrees divergence and passes through a linear polarizer. In the transmission mode (FIG. 10A) the polarized light passes through sample (110) to camera (112). The output signal from camera (112) is transferred to display (114). As shown, the angular signal in transmission exhibits bright main (116) and reference (118) lines over a dark background corresponding to the EOT peak position. In the reflection mode (FIG. 10B) the polarized light is reflected off sample (110) to camera (112). The output signal from camera (112) is transferred to display (114). As shown, the angular signal in reflection exhibits dark main (116) and reference (118) lines over a light background corresponding to the EOT dip. Because it is easier to measure the dark lines on a light background, the reflection mode is the preferred embodiment. In order to improve the precision the relative distance between the two lines (bright in case of transmission and dark in reflection mode) is measured. The length of the lines is determined by the number of pixels N in the camera, a fact that improves the line position determination by at least a factor of $\sqrt{N-1}$. Known algorithms for line detection can be applied such as the Hough transform, the Radon transform or the center of mass approach.

In an embodiment of the optical imaging setup of multi-element sensor for the angular mode of operation that consists of a TM polarized single wavelength source with diverging beam of up to few degrees divergence that is shown in FIG. 10A and FIG. 10B the source is an extended source. This embodiment is shown in FIG. 11A and FIG. 11B. In this case each point on the sensor is illuminated with the same angular spectrum. The beam incident on the sample is transmitted or reflected and passes through a Fourier transform lens where the angular spectrum in the Fourier plane is analyzed.

FIG. 11A and FIG. 11B schematically show an embodiment of the angular mode of operation in which the diverging beam is mainly diverging in the plane of incidence. The diverging beam can be obtained by several means: (a) highly astigmatic laser diode, (b) A beam from a point source (single mode fiber, pinhole, LED). FIG. 11A shows light emitted by a point source of light (120) that is collimated with a circular lens (122) and then focused to a focus line (126) using a positive cylindrical lens (124). As shown in FIG. 11B, the beam after the cylindrical focus diverges in the incidence plane more than in the perpendicular one.

Figure 12:
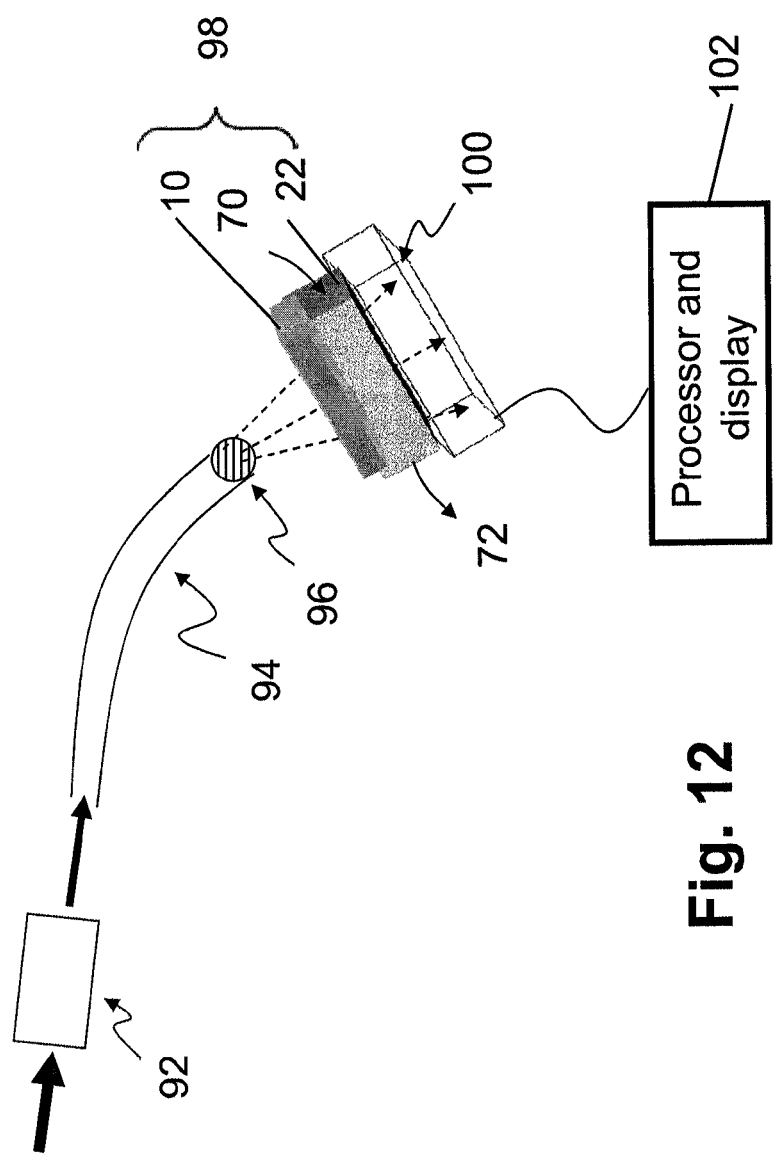
FIG. 12 schematically shows a fiber based imaging setup for making measurements based on the intensity and resonance angle location.

A fiber based imaging setup for making measurements based on the resonance angle is schematically shown in FIG. 12. Broadband light enters a tunable filter (92) and the exiting narrow band light enters an optical fiber (94) that has a polarizer (96) at its distal end. The polarized light spreads out and falls on sample 98, comprised of sensor (10) and analyte (22), which in this case flows through a flow cell as described in FIG. 6. The light that passes through the sample falls directly on a detector array or camera (100) whose output is sent to a processor and display unit 102.

Figure 13:
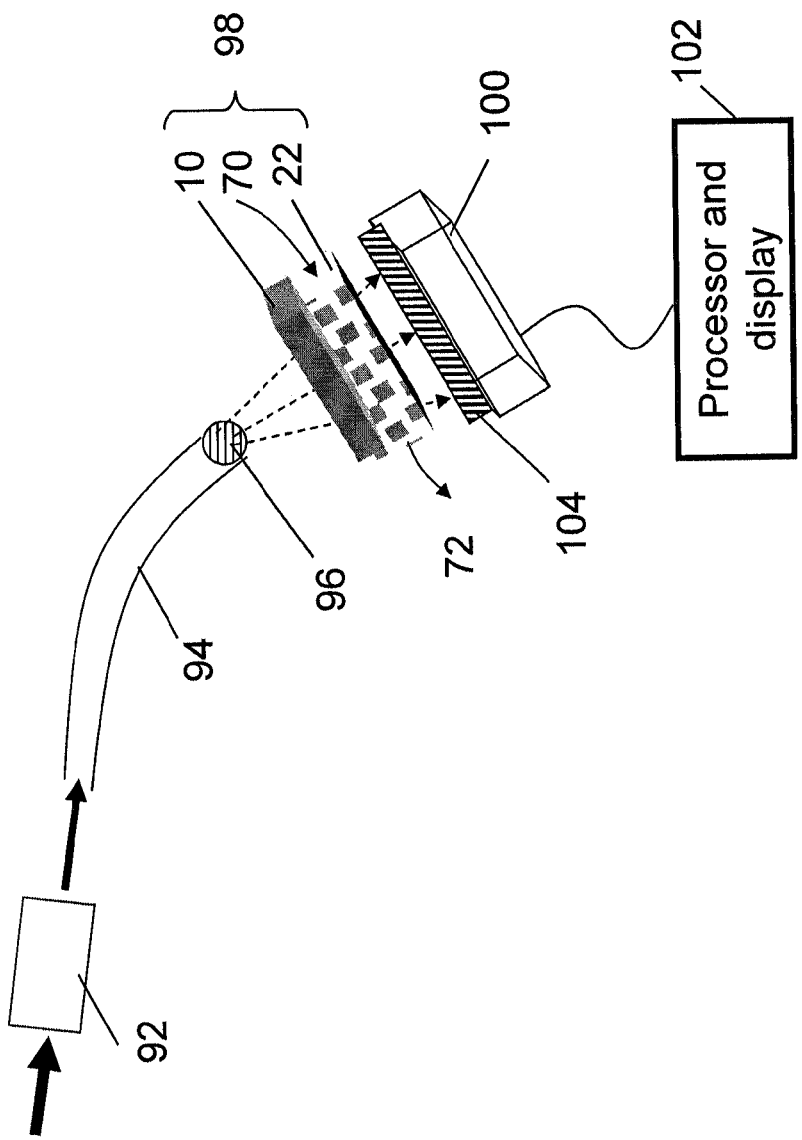
FIG. 13 schematically shows a fiber based imaging setup for making measurements based on the phase variations between the TM and TE waves.

A fiber based imaging setup for making measurements based on the phase variations is schematically shown in FIG. 13. In this case the setup is very similar to that in FIG. 12 with the exception that an analyzer (104) is placed in front of the detector array (100) and there is a space between sample (98) and analyzer (104).

Any of the optical setups described herein can be used to make measurements that are proportional to the phase retardation by polarizing the input beam at 45 degrees to the plane of incidence and passing the output beam through either a crossed or a parallel polarizer.

Any of the optical setups described herein can be used to make spectropolarimetric-ellipsometric measurements by polarizing the input beam at 45 degrees to the plane of incidence and passing the output beam through a rotating polarizer or through a polarization rotator, or a modulator followed by a fixed polarizer. The polarimetric or ellipsometric properties of the transmitted or reflected beams can then be extracted from a minimum of three measurements corresponding to three positions of the output polarizer or the polarization modulator.

Although embodiments of the invention have been described by way of illustration, it will be understood that the invention may be carried out with many variations, modifications, and adaptations, without exceeding the scope of the claims.

BIBLIOGRAPHY

1. Handbook of Biosensing and Biochips, edited by R. S. Marks, C. R. Lowe, D. C. Cullen, H. H. Weetall and I. Karube, John Wiley and Sons, 2007, ISBN978-0-470-01905-4.
2. I. Abdulhalim, M. Zourob, A. Lakhtakia, Overview of optical biosensing techniques, Invited chapter in the Handbook of Biosensing and Biochips, edited by R. S. Marks, C. R. Lowe, D. C. Cullen, H. H. Weetall and I. Karube, John Wiley and Sons, 2007, pages 413-446, ISBN978-0-470-01905-4.
3. Liedberg B, Nylander C and Sundstrom 1 (1983) Sens Actuators 4 299-304.
4. Homola J, Sinclair S and Gauglitz G Y (1999) Sens Actuators B 54 3-15.
5. Ebbesen T W, Lezec H J, Ghaemi H F, Thio T, and Wolff P A (1998) Nature 391667-669.
6. Bethe H A (1944) Phys Rev 66 163-182.
7. Lee K L, Wang K L, Wei P K (2007), Journal of Biomedical Optics, 12(4) 044023 doi: 10.1117/1.2772296.

8. Lee K L, Wang K L, Wei. PK (2008) Plasmonics 3 119-125.
9. Garcia-Vidal F J, Lezec H J, Ebbesen T W, and Martin-Moreno L (2003) Phys Rev Lett 90 213901.
10. Ma J, Liu S, Zhang D, Yao J, Xu C, Shao J, Jin Y and Fan Z, J. (2008) Opt. A: Pure Appl. Opt. 10 035002.
11. Rajan, Chand S and Gupta B D (2006) Sens Actu B 115 344.
12. Brolo A G, Gordon R, Leathem B, Kavanagh K L (2004) Langmuir 20 (12) 4813-4815.
13. Karabchevsky A, Krasnyakov O, Abdulhalim I, Hadad B, Goldner A, Auslender M, Hava S (2009) Photonics and Nanostructures—Fundamental and Applications 7, 170-175.
14. Abdulhalim Zourob M D and Lakhtakia A (2008) Electromagnetics 28 214-242.
15. Ding Y, Cao Z Q and Shen Q S (2003) Optical and Quantum Electronics 35 1091-1097.
16. Cao Q, Lalanne P (2002) Phys Rev Lett 88 057403 doi: 0.1103/PhysRevLett. 88.057403
17. Fan W, Zhang S, Minhas B, Malloy K L, Brueck R J (2005) Phys Rev Lett 94 033902.
18. I. Abdulhalim, Biosensing configurations using guided wave resonant structures, in NATO Science for Peace and Security Series B: Physic sand Biophysics, Optical waveguide sensing and imaging, Ch. 9, pp. 211-228, Editors: Wojtek J. Bock, Israel Gannot and Stoyan Taney, Springer-Verlag, Amsterdam, Netherlands, December 2008.
19. A. Shalabney and I. Abdulhalim, Electromagnetic fields distribution in multilayer thin film structures and the origin of sensitivity enhancement in surface plasmon resonance sensors, Sensors and Actuators A, 159, 24-32 (2010).
20. Krasnykov O, Karabchevsky A, Shalabney A, Auslender M and Abdulhalim I, Sensor with Increased Sensitivity Based on Enhanced Optical Transmission in the Infrared, Opt. Commu. 284, 1435-1438 (2011).
21. Karabchevsky A, Krasnykov O, Auslender M, Hadad B, Goldner A and Abdulhalim I, Theoretical and Experimental Investigation of Enhanced Transmission Through Periodic Metal Nanoslits for Sensing in Water Environment, Journal of Plasmonics, 4, 281-292 (2009).
22. Karabchevsky A, Krasnykov O, Abdulhalim I, Hadad B, Goldner A, Auslender M and Hava S, Metal Grating on a Substrate Nanostructure for Sensor Applications, Photon Nanostruct: Fundam Appl 7, 170-175 (2009).
23. Karabchevsky A, Auslender M and Abdulhalim I, Dual LSPR Excitation at the Interfaces of Periodic Metallic Nanostructures, J. Nano Photonics 5, 051821-9p (2011).
24. I. R. Hooper and J. R. Sambles, Differential Ellipsometric Surface Plasmon Resonance Sensors with Liquid Crystal Polarization Modulators, Appl. Phys. Lett. 85, 3017-19 (2004).
25. Wei-Liang Hsu, Shu-Sheng Lee, Chih-Kung Lee, Ellipsometric Surface Plasmon Resonance, Journal of Biomedical Optics 14, 024036 (8 pp) (2009)].

The invention claimed is:

1. A surface plasmon resonance (SPR) sensor to determine the presence and quantity of biological or chemical entities in an analyte, said sensor comprising:
a metal periodic structure deposited as a thin layer of a noble metal, comprising a one dimensional array of nanoslits or a two dimensional array of nanoholes on a transparent dielectric substrate;
a nm-thick layer of transparent dielectric protection layer on top of the metal periodic structure; and
a functionalization layer, which acts as a binding layer to biological or chemical entities in an analyte that is in contact with the functionaliztion layer;
wherein:
the spaces perforated in the metal are at least partially filled by a material with a refractive index as close as possible to that of the substrate;
the thickness of the metal layer is no more than 100 nm;
the refractive index, transparency and the thickness of the dielectric protection nanolayer are chosen so that it does not affect the sensor sensitivity;
the thickness of the dielectric protection layer is no more than 20 nm; and
the presence of the material in the spaces perforated in the metal distances the analyte material from the metal-substrate interface, thereby improving the signal to noise ratio for the spectral/angular peak corresponding to the plasmon excited at the metal-substrate interface allowing this spectral peak to be used as a reference relative to which the spectral peaks corresponding to the plasmon excited at the metal-analyte interface is measured.

2. The sensor of claim 1, wherein the period of the metal structure is larger than 600 nm.

3. The sensor of claim 1, wherein the material that at least partially fills the spaces perforated in the metal have the same thermooptic coefficient as the analyte.

4. The sensor of claim 1, wherein the difference between the refractive index of the substrate and analyte is at least 0.1.

5. The sensor of claim 1, wherein an anti-reflection coating is added on an external surface of the substrate.

6. The sensor of claim 1, comprising dielectric spacers that hold a transparent glass plate parallel to the protection layer with a gap having less than 200 microns thickness between the glass plate and the protection layer, said gap forming a channel through which a liquid analyte can be contained or flow.

7. The sensor of claim 6, comprising at least one of:
antireflection coatings covering the transparent glass plate; and
a transparent electrode coated on the side of the transparent glass plate facing the analyte, thereby allowing an electric field to be applied between the metal periodic structure and the top glass plate.

8. An array comprised of a plurality of sensors of claim 1, wherein each of the sensors in the array is constructed on a common substrate and each of the sensors has dimensions equal to at least twenty times the period of the spacing between the adjacent nanoslits or the distance between adjacent nanoholes.

9. The array of claim 8 wherein the functionalization layer of at least one of the sensors is different from the functionalization layer of other sensors in the array.

10. The array of claim 8 wherein the period in each sensor or group of sensors in the array is different from the period of other sensors or group of sensors in the array so that each sensor or group of sensors will be monitored with slightly different spectral or angular range.

11. The array of claim 8, wherein the sensor plane is imaged on a camera and the wavelength is controlled by a tunable source, using a tunable filter or monochromator.

12. A method for determining the presence and quantity of biological or chemical entities in an analyte, the method comprising:

irradiating an analyte covered sensor of claim 1 with TM polarized light using an optical setup comprising a light source, lens system, and polarizer;

measuring the resonance wavelength or incidence angle of the resonant transmission peaks or reflection dips of the plasmon excited at the metal-analyte interface relative to the resonance wavelength or incidence angle of the resonant transmission peaks or reflection dips of the plasmon excited at the metal-substrate interface; and determining the presence and quantity of biological or chemical entities in the analyte.

13. A method for determining the presence and quantity of biological or chemical entities in an analyte, the method comprising:

irradiating an analyte covered sensor of claim 1 with an input beam polarized at 45 degrees to the plane of incidence using an optical setup comprising a light source, lens system, and polarizer;

passing the output beam through either a crossed or a parallel polarizer;

measuring the phase retardation between TE and TM waves of the plasmon excited at the metal-analyte interface that are incident on the sensor relative to the phase retardation between TE and TM waves of the plasmon excited at the metal-substrate interface that are incident on the sensor; and determining the presence and quantity of biological or chemical entities in the analyte.

14. A method for determining the presence and quantity of biological or chemical entities in an analyte, the method comprising:

irradiating an analyte covered sensor of claim 1 with an input beam polarized at 45 degrees to the plane of incidence using an optical setup comprising a light source, lens system, and polarizer;

passing the output beam through either a rotating polarizer, a polarization rotator followed by a fixed polarizer, or a phase modulator followed by a fixed polarizer;

extracting the polarimetric or ellipsometric properties of the transmitted or reflected beams corresponding to the resonance wavelengths or angles of the plasmon excited at the metal-analyte interface relative to the ellipsometric or polarimetric properties of the same beams corresponding to resonance wavelengths or angles of the plasmon excited at the metal-substrate interface; and determining the presence and quantity of biological or chemical entities in the analyte.

15. The method of claim 14, wherein the polarimetric or ellipsometric properties of the transmitted or reflected beams are extracted from a minimum of three measurements corresponding to three positions of the output polarizer or the polarization modulator.

16. A method for determining the presence and quantity of biological or chemical entities in an analyte, the method comprising:

irradiating, using an optical setup comprising a light source, lens system, and polarizer, an analyte covered sensor of claim 1 with an incoming beam of light that has passed through an input polarizer oriented to the TM orientation, wherein the input beam is a single wavelength diverging beam with few degrees divergence;

directing the output beam that passes through or is reflected from the analyte covered sensor to a detector array or a camera;

measuring on the output of the detector array or camera a dark line on a bright background in the reflected beam or a bright line on a dark background in the transmitted beam corresponding to the plasmon excited at the metal analyte interface relative to a dark line on a bright background in the reflected beam or a bright line on a dark background in the transmitted beam corresponding to the plasmon excited at the metal substrate interface; and determining the presence and quantity of biological or chemical entities in the analyte.

* * * * *